United States Patent
Miyazawa et al.

(10) Patent No.: US 7,036,503 B2
(45) Date of Patent: May 2, 2006

(54) FACE-WEARING HUMIDIFIER

(75) Inventors: Kiyoshi Miyazawa, Kagawa (JP);
Takeshi Hanajiri, Kagawa (JP);
Hiromi Teraoka, Mitoyo-gun (JP);
Naohito Takeuchi, Kagawa (JP)

(73) Assignee: Uni-Charm Corporation, Shikokuchuo (JP)

( * ) Notice: Subject to any disclaimer, the term of this patent is extended or adjusted under 35 U.S.C. 154(b) by 0 days.

(21) Appl. No.: 11/035,226

(22) Filed: Jan. 12, 2005

(65) Prior Publication Data
US 2005/0145250 A1    Jul. 7, 2005

Related U.S. Application Data

(63) Continuation of application No. PCT/JP04/08045, filed on Jun. 9, 2004.

(30) Foreign Application Priority Data

Jun. 9, 2003    (JP)    ............... 2003-163137

(51) Int. Cl.
*A62B 18/08*    (2006.01)
(52) U.S. Cl. .................... 128/201.13; 128/204.17; 128/206.19
(58) Field of Classification Search ........... 128/201.13, 128/204.17, 206.19; 607/114, 112, 109–111, 607/96, 99, 104, 108
See application file for complete search history.

(56) References Cited

U.S. PATENT DOCUMENTS 6,096,067 A * 8/2000 Cramer et al. ............... 607/96
6,409,746 B1 * 6/2002 Igaki et al. .................. 607/109
6,824,557 B1 * 11/2004 Tone et al. .................. 607/114

FOREIGN PATENT DOCUMENTS

| EP | 1147752 A1 * | 10/2001 |
|---|---|---|
| JP | 56-85336 A | 7/1981 |
| JP | 4-32714 | 3/1992 |
| JP | 7-43329 | 8/1995 |
| JP | 7-213549 | 8/1995 |
| JP | 7-49937 Y2 | 11/1995 |
| JP | 8-231386 | 9/1996 |
| JP | 3049707 B2 | 6/2000 |
| JP | 3121316 B2 | 12/2000 |
| JP | 2002-78728 | 3/2002 |

OTHER PUBLICATIONS

Patent Abstracts of Japan for JP07-213549 published on Aug. 15, 1995.
Patent Abstracts of Japan for JP08-231386 published on Sep. 10, 1996.
International Search Report for PCT/JP2004/008045 mailed on Sep. 28, 2004.

* cited by examiner

*Primary Examiner*—Mital Patel
(74) *Attorney, Agent, or Firm*—Darby & Darby

(57) ABSTRACT

A humidifier having a heat-generating composition for generating steam is disclosed. The humidifier is permitted to fit the face, keeping the humidity high at a space between the face and the humidifier for many hours. A central non heat-generating belt, which functions as a flexible belt, is provided between inner heat-generating regions containing heat-generating composition. Lateral non heat-generating belts, which function as a flexible belt, are provided between the inner heat-generating regions and outer heat-generating regions. The humidifier fits the face by deforming the flexible belts. Thus, the face is kept moisturized by steam discharged from the inner heat-generating regions and the outer heat-generating regions.

7 Claims, 3 Drawing Sheets

FACE-WEARING HUMIDIFIER

CROSS-REFERENCE TO PRIOR APPLICATION

This application is a Continuation of International Patent Application Serial No. PCT/JP2004/008045 filed Jun. 9, 2004 which claims the benefit of priority from Japanese Patent Application No. 2002-163137 filed Jun. 9, 2003 both of which are incorporated by reference herein in their entireties. The International Application was published in Japanese on Dec. 16, 2004 as WO 2004/108030 A1 under PCT Article 21(2).

BACKGROUND OF THE INVENTION

1. Field of the Invention

The present invention relates to a face-wearing humidifier which can apply steam to a face during wear to exhibit a moisturizing effect on the face.

2. Related Art

In Japanese Patent No. 3049707 (Patent Publication 1), there is disclosed an invention concerning steam-generating device for applying steam to the skin of the human body. The steam-generating device includes a steam-generating composition which discharges steam when metal powder is oxidized, and a temperature control member and a moisture-permeable sheet are disposed on a skin-side of the steam-generating composition. The temperature control member is formed of a nonwoven fabric, paper, apertured foamed plastic or the like, so that the steam discharged from the steam-generating composition is cooled by the temperature control member and then passes through the moisture-permeable sheet for subsequent application to the skin.

In Japanese Unexamined Patent Publication No. H07-213549 and Japanese Unexamined Patent Publication No. H08-231386 (Patent Publications 2 and 3, respectively), on the other hand, there are disclosed inventions concerning disposable body warmer and thermal plaster to be placed on the skin of the human body.

In these inventions, a heat-generating composition which generates heat when metal powder is oxidized is divided into separate groups and housed in a flat bag which is wholly or partially formed of a stretchable sheet. In addition, the bag can be adhered to the skin through a pressure-sensitive adhesive layer. When adhered to a joint of the human body, such a disposable body warmer and a thermal plaster can warm up the joint by heat generated from the heat-generating composition, and because the heat-generating composition is divided into separate groups, bending at the joint can be easily performed.

Patent Publication 1 discloses that a steam-generating composition gives steam to the skin of the human body such as scalp, shoulder, neck, face, buttocks, legs, hands and arms, or to the mucous membrane such as of eyes, nose and throat. However, it does not describe how the steam-generating composition is shaped to fit contours of the face when used on the face.

Patent Publications 2 and 3 disclose to divide the heat-generating composition, which only aims at adhering the heat-generating composition to a joint of the human body to follow the bending motion at the joint without intending to enable the worn humidifier to easily fit contours of the face.

SUMMARY OF THE INVENTION

The present invention is to solve the foregoing problems in the prior art and has an object to provide a face-wearing humidifier which is easy to fit contours of the face and prevents escape of steam applied to the face so as to improve a moisturizing effect.

According to an implementation of the present invention, there is provided a face-wearing humidifier comprising a moisture-permeable skin-side surface sheet to be directed toward a skin, an outer surface sheet to be directed outward, and a heat-generating composition.

The humidifier is symmetrical or generally symmetrical about a longitudinal centerline and includes a central non heat-generating belt extending along the longitudinal centerline, a pair of inner heat-generating regions located laterally and symmetrically outside the central non heat-generating belt, lateral non heat-generating belts located laterally outside the inner heat-generating regions and extending longitudinally in parallel or not in parallel with but disposed symmetrically about the central non heat-generating belt, and outer heat-generating regions located laterally outside the lateral non heat-generating belts but symmetrically about the central non heat-generating belt.

The heat-generating composition for generating steam is interposed between the skin-side surface sheet and the outer surface sheet in the inner heat-generating regions and the outer heat-generating regions, whereas the heat-generating composition is not present in the central non heat-generating belt and the lateral non heat-generating belts.

With the skin-side surface sheet being directed toward the face and the central non heat-generating belt being located centrally and longitudinally of the face, the humidifier is deformable around the central non heat-generating belt and the lateral non heat-generating belts so as to follow the shape of the face.

The face-wearing humidifier according to an implementation of the present invention is allowed to easily bend at the central non heat-generating belt and the lateral non heat-generating belts. Even after the heat-generating composition is stiffened through oxidation, therefore, the non heat-generating belts enable the humidifier to be deformed to have a concave skin-side, following the contours of the face. This results in inhibiting steam discharged into the space between the humidifier and the face from escaping to the outside, thereby providing a good moisturizing effect on the face skin for many hours.

Also according to an implementation of the present invention, the humidifier may have a peripheral edge bowed laterally outward with respect to the longitudinal centerline, wherein an upper portion above a lateral centerline may have a larger area than a lower portion below the lateral centerline.

Since the peripheral edge of the humidifier is bowed laterally outward and the upper portion has a large area, the humidifier is easy to fit the cheeks of the face, and also since the lower portion has a small area, the humidifier easily fits the region from mouth to jaw.

Also according to an implementation of the present invention, at least the skin-side surface sheet and the outer surface sheet may be joined together in the central non heat-generating belt and the lateral non heat-generating belts, and at least the skin-side surface sheet and the outer surface sheet may be joined together also in a given width of a peripheral belt extending all along the peripheral edge.

In the humidifier, since the flexible peripheral belt without the heat-generating composition is provided in a given width along the peripheral edge, the peripheral belt makes the humidifier deformable to follow the contours of the face. Therefore the humidifier is less apt to form a gap between the peripheral edge and the face, which results in preventing escape of steam to the outside.

Furthermore, according to an implementation of the present invention, the lateral belts in which at least the skin-side surface sheet and the outer surface sheet are joined together may be provided laterally outside the lateral non heat-generating belts to extend laterally below the outer heat-generating regions, wherein non heat-generating regions which are defined between the lateral belts and the peripheral belt and in which the heat-generating composition is not present may be provided below the outer heat-generating regions.

Since the non heat-generating regions without the heat-generating composition is provided below the outer heat-generating regions, the relatively flexible non heat-generating regions are directed to the region below the cheeks and make the humidifier deformable to follow the hollow shape below the cheeks. This prevents formation of an excess gap between the humidifier and the cheeks, so that the steam is less apt to escape from between the humidifier and the cheeks.

Also according to an implementation of the present invention, it is preferred that a foamed plastic sheet with steam passages passing through it from the top to the bottom and closed cells formed therein is disposed between the heat-generating composition and the skin-side surface sheet.

The foamed plastic sheet acts as a heat insulator which lowers the temperature of steam from the heat-generating composition so that the steam can be applied to the skin at an optimum temperature. In addition, the steam passages formed in the foamed plastic sheet allow a lot of steam to be discharged toward the face, as well as a rapid temperature rise of the heat-generating composition to a desired degree when the humidifier is unpacked from a sealed package, because a lot of oxygen can be applied to the heat-generating composition through the steam passages.

According to an implementation of the present invention, the heat-generating composition may comprise metal powder, a salt, a water retention agent and moisture.

The water retention agent enables prolonged moisture retention, which results in prolonged steam application.

Further according to an implementation of the present invention, the heat-generating composition may comprise carbon for facilitating oxidation of the metal powder.

The carbon facilitates oxidation of the metal powder, so that the heat-generating composition can be kept at a suitable temperature for many hours.

According to an implementation of the present invention, as has been described hereinabove, the humidifier containing the heat-generating composition for steam generation easily comes into close contact with the face and steam is less apt to escape to the outside from between the face and the humidifier, so that the face can always be kept moisturized.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

Figure 1:
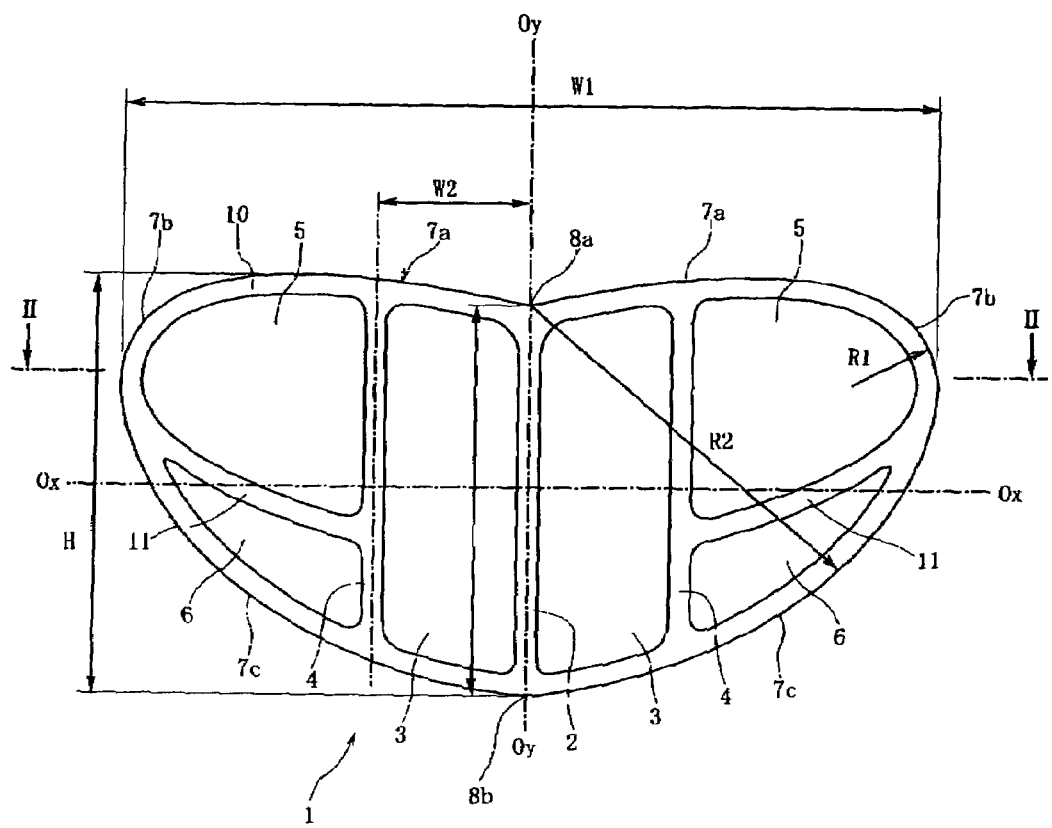
FIG. 1 is a rear view showing one embodiment of a humidifier of the invention from its skin-side.
Figure 2:
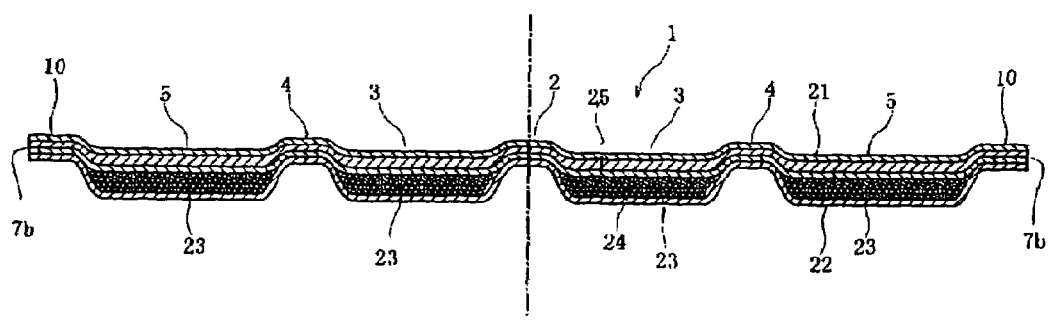
FIG. 2 is a cross-sectional view taken along arrowed line II—II of FIG. 1.
Figure 3:
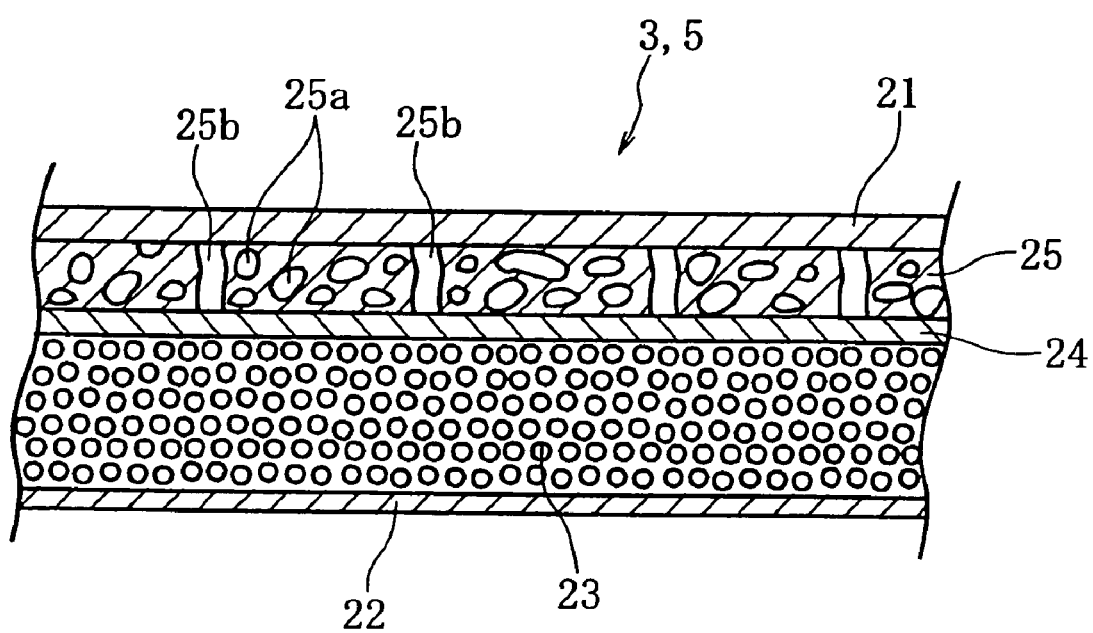
FIG. 3 is an enlarged sectional view of a heat-generating region.

FIG. 1 is a rear view in which a disposable face-wearing humidifier according to one embodiment of the present invention is viewed from a skin-side to be directed toward a face; FIG. 2 is a cross-sectional view taken along arrowed line II—II of FIG. 1; FIG. 3 is an enlarged sectional view of a heat-generating region; and FIG. 3 is a front view showing a state where the humidifier is worn on the face.

Referring to FIG. 1, a humidifier 1 is symmetrical about a longitudinal centerline Oy—Oy, with which the humidifier is separated into right and left portions, and asymmetrical about a lateral centerline Ox—Ox, with which the humidifier is separated into upper and lower portions.

The humidifier 1 is provided with a central non heat-generating belt 2 along the longitudinal centerline Oy—Oy. The central non heat-generating belt 2 is formed in a straight line of a fixed width. Laterally outside the central non heat-generating belt 2, inner heat-generating regions 3, 3 are located, and further laterally outside thereof, lateral non heat-generating belts 4, 4 are located to extend longitudinally. In the present embodiment, the non heat-generating belts 4, 4 run parallel to the central non heat-generating belt 2 and are longitudinally provided in a straight line of a fixed width. However, the non heat-generating belts 4, 4 may be formed in a straight line unparallel to the central non heat-generating belt 2 or in a curved line unparallel to the central non heat-generating belt 2.

Laterally outside the lateral non heat-generating belts 4, 4 and in the upper portion, outer heat-generating regions 5, 5 are located. Below the outer heat-generating regions 5, 5 and laterally outside the lateral non heat-generating belts 4, 4, non heat-generating regions 6, 6 are provided.

The humidifier 1 is shaped to have a peripheral edge which consists of upper peripheral edges 7a, 7a extending laterally outwardly from an upper end 8a located on the longitudinal centerline Oy—Oy along gentle convex curves, lateral peripheral edges 7b, 7b bowed laterally outwardly along convex curves with a smaller radius of curvature R1 than that of the upper peripheral edges 7a, 7a and lower peripheral edges 7c, 7c extending along convex curves with a larger radius of curvature R2 than that of the lateral peripheral edges 7b, 7b to a lower end 8b on the longitudinal centerline Oy—Oy.

Thus, in the humidifier 1, the portion above the lateral centerline Ox—Ox has a larger area than the portion below the lateral centerline Ox—Ox.

A given width of a peripheral belt 10 extends all along the upper peripheral edges 7a, 7a, the lateral peripheral edges 7b, 7b and the lower peripheral edges 7c, 7c. Moreover, lateral belts 11, 11 extend laterally between the outer heat-generating regions 5, 5 and the non heat-generating regions 6, 6.

The inner heat-generating regions 3, 3 are enclosed by the central non heat-generating belt 2, the lateral non heat-generating belt 4, and the peripheral belts 10, 10 which respectively lie on top and bottom thereof. The outer heat-generating regions 5, 5 are enclosed by the lateral non heat-generating belt 4, the peripheral belt 10 and the lateral belt 11. Also, the non heat-generating region 6 is enclosed by the peripheral belt 10, the lateral non heat-generating belt 4 and the lateral belt 11.

As shown in the cross-sectional view of FIG. 2, the humidifier 1 is provided with a moisture-permeable skin-side surface sheet 21 on the skin-side to be directed toward the face and a moisture-impermeable outer surface sheet 22 on an outer-side. In the inner heat-generating regions 3, 3 and the outer heat-generating regions 5, 5, a heat-generating composition 23 for generating steam is disposed inside the outer surface sheet 22. On the skin-side of the heat-generating composition 23 is disposed a moisture-permeable inner sheet 24 for preventing leakage of the heat-generating composition 23, and between the inner sheet 24 and the skin-side surface sheet 21 a heat insulator 25 is interposed.

The heat-generating composition 23 is provided only in the inner heat-generating regions 3, 3 and the outer heat-generating regions 5, 5. All the skin-side surface sheet 21, the outer surface sheet 22, the inner sheet 24 and the heat insulator 25 are coextensive with the overall shape of the humidifier 1. In the central non heat-generating belt 2, the lateral non heat-generating belts 4, 4, the peripheral belt 10 and the lateral belt 11, on the other hand, the skin-side surface sheet 21, the outer surface sheet 22, the inner sheet 24 and the heat insulator 25 are stacked in layers and bonded together without the heat-generating composition 23.

The skin-side surface sheet 21, the outer surface sheet 22, the inner sheet 24 and the heat insulator 25 are bonded together under pressure with a hot-melt adhesive applied therebetween. Alternatively, if the individual fabrics contain thermoplastic resin, they may be heated under pressure to be heat sealed at the belts 2, 4, 10 and 11. In the non heat-generating regions 6, 6, on the other hand, the skin-side surface sheet 21, the outer surface sheet 22, the inner sheet 24 and the heat insulator 25 are stacked in layers without being bonded together.

Hence, the central non heat-generating belt 2 and the lateral non heat-generating belt 4, 4 function as a flexible belt, or both edges of the non heat-generating belts 2, 4, 4 function as a flexible line. The lateral belts 11, 11 also function as a flexible belt or a flexible line.

The skin-side surface sheet 21 may be a spunlaced nonwoven fabric formed of rayon and pulp, rayon and cotton, etc., or a resin film formed with pores which allow passage of steam, such as polyethylene or polypropylene.

The outer surface sheet 22 may be a moisture-impermeable resin film, such as polyethylene or polypropylene film. In an alternative, there may be used an ethylene/vinyl alcohol copolymer (EVOH) or vinylidene chloride (PVDC) single layer film having air barrier function or a multilayer film containing it. In another alternative, a spunlaced nonwoven fabric or the like may be laminated to the exterior surface of the moisture-impermeable resin film to improve the appearance of the outer surface sheet 22. In still another alternative, the outer surface sheet 22 may be a moisture-permeable resin film or a moisture-permeable nonwoven fabric. However, in order to discharge steam effectively to the face, it is preferable that the outer surface sheet 22 is moisture-impermeable.

The heat-generating composition 23 contains metal powder, a salt for corrosion and oxidation of the metal powder, and moisture. It also contains a moisture retention agent for prolonged moisture retention, as well as carbon for facilitating oxidation of the metal powder. The metal powder may be iron, aluminum or zinc. The salt may be sodium chloride, potassium chloride, calcium chloride or magnesium chloride. The moisture retention agent may be vermiculite, calcium silicate, silica gel or silica. The carbon may be activated carbon, carbon black or graphite.

The inner sheet 24 is a moisture-permeable sheet and provided inside the outer surface sheet 22 so as to prevent leakage of each constituent of the heat-generating composition 23. The inner sheet 24 may be a spunbonded nonwoven fabric, a melt-blown nonwoven fabric or a composite nonwoven fabric in which a spunbonded nonwoven fabric, a melt-blown nonwoven fabric, and a spunbonded nonwoven fabric are laminated in this order.

The heat insulator 25 has heat-insulating property due to air contained therein and also is permeable to steam discharged from the heat generating composition 23. In this embodiment, the heat insulator is made of a foamed plastic sheet. As shown in FIG. 3, the foamed plastic sheet has a large number of closed cells 25a and also a large number of steam passages 25b passing through it from the top to the bottom The foamed plastic sheet, such as polyethylene foam sheet, polypropylene foam sheet or urethane foam sheet, has an expansion ratio of 20 to 30 times, wherein apertures having a diameter of 0.1 to 5 mm are formed with an aperture area ratio in the range of 5 to 60% to function as the steam passages 25b.

Alternatively, a laminate of a plurality of spunlaced nonwoven fabrics or a laminate of a spunlaced nonwoven fabric and a paper may be used for the heat insulator 25.

As shown in FIG. 2, the skin-side surface sheet 21 and the outer surface sheet 22 are bowed slightly outward in the inner heat-generating regions 3, 3, the outer heat-generating regions 5, 5, and the non heat-generating regions 6, 6. Therefore, a proper space is always created between the skin and the skin-side surface sheet 21 when the humidifier is worn on the face.

Figure 4:
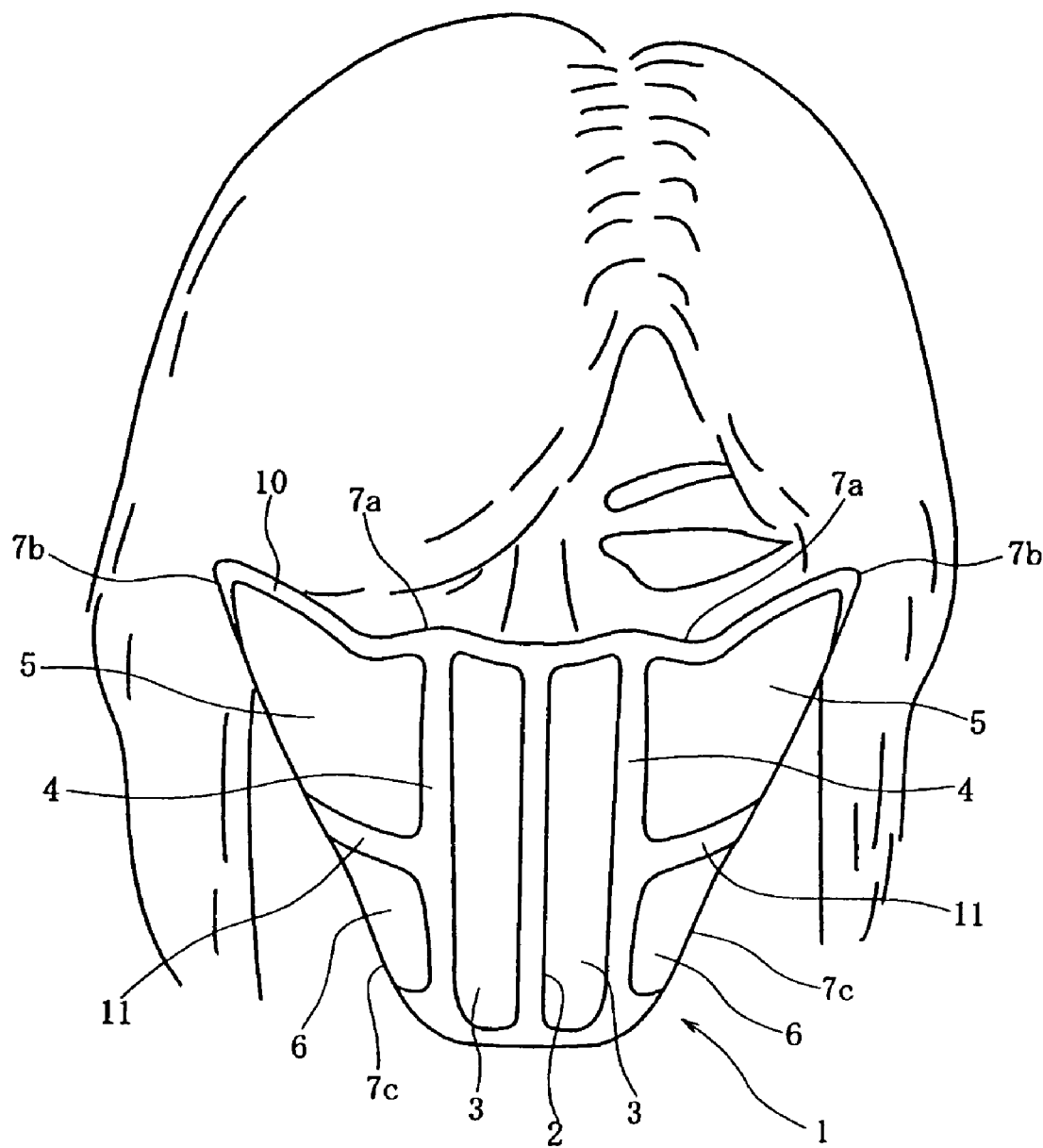
FIG. 4 is a front view showing a state where the humidifier of FIG. 1 is worn on the face.

As shown in FIG. 4, the humidifier 1 is worn to cover across the jaw, cheeks and nose with the central non heat-generating belt set on the face axis or the ridge of the nose. When thus worn, the central non heat-generating belt 2 and the lateral non heat-generating belts 4, 4 function as a flexible belt to facilitate bending of the humidifier, so that the portion located between the opposite lateral non heat-generating belts 4, 4 can easily fit to the ridge and both sides of the nose. Further, since the lateral belts 11, 11 also function as a flexible belt, the outer heat-generating regions 5, 5 and the non heat-generating regions 6, 6 are allowed to be deformed in conformity with the shape of the cheeks from top to bottom, which results in easy fit to the cheeks.

Here, since the peripheral belt 10 is soft and flexible, the peripheral belt 10 in contact with the face is less apt to give an unpleasant feeling. In addition, the peripheral belt 10 can easily conform to irregularities of the face to close the space between the face and the skin-side surface sheet 21.

The humidifier 1 may be held by extending elasticized straps or strings from the lateral peripheral edges 7b, 7b to opposite sides and then hanging them on the ears or by wearing a conventional mask to cover the outer side of the humidifier 1 being worn as shown in FIG. 4. In an alternative, a pressure-sensitive adhesive layer may be provided on a skin-side inner surface of the peripheral belt 10 so as to enable adhesion of the peripheral belt 10 to the face. In another alternative, the humidifier 1 may be held by hand in the state of FIG. 4 until applying steam to the skin is completed.

The humidifier 1 is packed in a sealed bag formed of a moisture-permeable film or the like. The bag is unsealed before use and the humidifier 1 is taken out and worn on the face as shown in FIG. 4. When the humidifier 1 removed from the bag is exposed to air, the air is supplied from the skin-side surface sheet 21 through the heat insulator 25 to the heat generating composition 23; oxidation reaction of the metal powder generates heat and then moisture contained in the heat generating composition 23 and in the moisture retention agent turns to steam. The steam passes through the steam passages 25b of the heat insulator 25 and diffuses through the skin-side surface sheet 21 to be applied to the face.

Here, since the heat insulator 25 has a heat insulating effect, heat generated by the heat generating composition 23 can be blocked to prevent extreme temperature rise in the space between the face and the humidifier 1, controlling the temperature preferably equal to or less than 50 degrees centigrade. Therefore, when steam is applied to the face, feeling too hot to the face skin can be prevented.

As described above, since the humidifier 1 easily fits to the face so that the steam keeps high the humidity in the space between the face and the humidifier 1, the moisturizing effect can be performed on the skin, and also blood circulation of the skin can be improved so as to be effective in facial beauty treatment and skin cleansing.

Here, an additional moisture retention agent may be disposed in the heat generating composition 23 of the humidifier 1, or between the inner sheet 24 and the heat insulator 25, or between the heat insulator 25 and the skin-side surface sheet; a skin lotion, an aromatic substance, etc. may be present in the heat generating composition 23 of the humidifier 1 or between the inner sheet 24 and the heat insulator 25, or between the heat insulator 25 and the skin-side surface sheet.

Next, the humidifier 1 has a maximum width W1 preferably in the range of 180 to 300 mm and a longitudinal dimension H preferably in the range of 100 to 200 mm. However, this invention should not be construed as limited to the said dimensions.

In the humidifier 1, oxidation of the heat-generating composition 23 liberates heat, which causes each material constituting the heat-generating composition to cling together and harden the inner heat-generating regions 3, 3 and the outer heat-generating regions 5, 5. However, the humidifier 1 can easily fit to the face's nose as shown in FIG. 4 if a width W2 between centerlines of the central non heat-generating belt 2 and the lateral non heat-generating belt 4 is set to an optimum size.

EXAMPLES

In this regard, a fit test was carried out using an actually made humidifier of FIG. 1. The dimensions of the humidifier 1 were as follows: the maximum width W1 was 230 mm, the longitudinal dimension H was 135 mm, the radius of curvature R1 of the lateral peripheral edge 7b was 20 mm, and the radius of curvature R2 of the lower peripheral edge 7c was 65 mm.

Various humidifiers were prepared with the width W2 between centerlines of the central non heat-generating belt 2 and the lateral non heat-generating belt 4 set to 10 mm, 20 mm, 40 mm, 60 mm or 70 mm, and applied on ten females' faces to conduct a sensory test for fit. Symbols "⊚", "○", "Δ" and "X" designated "fitting well", "fitting loosely", "neither fitting well nor badly" and "fitting badly", respectively. Test results were as follows:

10 mm: Evaluated as Δ by five subjects and X by the other five.
20 mm: Evaluated as ○ by eight subjects and Δ by the other two.
40 mm: Evaluated as ⊚ by eight subjects and ○ by the other two.
60 mm: Evaluated as ○ by seven subjects and Δ by the other three.
70 mm: Evaluated as Δ by five subjects and X by the other five.

From the above, it is seen that the width W2 between centerlines of the central non heat-generating belt 2 and the lateral non heat-generating belt 4 preferably falls within the range of 15 mm to 65 mm, more preferably within the range of 20 mm to 60 mm. In the case where the central non heat-generating belt 2 and the lateral non heat-generating belt 4 are unparallel, the preferred range of the mean width measured between centers thereof is the same as the above.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the features set out in the appended claims.

What is claimed is:

1. A face-wearing humidifier being generally symmetrical about a longitudinal center line, comprising:
   a moisture-permeable skin-side surface sheet to be directed toward a skin;
   an outer surface sheet to be directed outward;
   a heat-generating composition for generating steam, said composition interposed between the skin-side surface sheet and the outer surface sheet,
   wherein the humidifier is divided into:
   a central non heat-generating belt extending along the longitudinal centerline;
   a pair of inner heat-generating regions located laterally outside but symmetrically about the central non heat-generating belt;
   lateral non heat-generating belts located laterally outside the inner heat-generating regions and extending longitudinally in parallel or not in parallel with but disposed symmetrically about the central non heat-generating belt; and
   outer heat-generating regions located laterally outside the lateral non heat-generating belts but symmetrically about the central non heat-generating belt,
   wherein the heat-generating composition, interposed between the skin-side surface sheet and the outer surface sheet, is disposed in the inner heat-generating regions and the outer heat-generating regions but not disposed in the central non heat-generating belt and the lateral non heat-generating belts, wherein the humidifier is deformable around the central non heat-generating belt and the lateral non heat-generating belts to follow the shape of a face.

2. A face-wearing humidifier according to claim 1, wherein the humidifier has a peripheral edge bowed laterally outward with respect to the longitudinal centerline, wherein an upper portion above a lateral centerline has a larger area than a lower portion below the lateral centerline.

3. A face-wearing humidifier according to claim 1, wherein at least the skin-side surface sheet and the outer surface sheet are joined together in the central non heat-generating belt and the lateral non heat-generating belts, and at least the skin-side surface sheet and the outer surface sheet are joined together also in a given width of a peripheral belt extending all along the peripheral edge.

4. A face-wearing humidifier according to claim 1, wherein lateral belts in which at least the skin-side surface sheet and the outer surface sheet are joined together are provided laterally outside the lateral non heat-generating belts to extend laterally below the outer heat-generating regions, wherein non heat-generating regions which are defined between the lateral belts and the peripheral belt and in which the heat-generating composition is not present are provided below the outer heat-generating regions.

5. A face-wearing humidifier according to claim 1, wherein a foamed plastic sheet with steam passages passing through it from the top to the bottom and closed cells formed therein is disposed between the heat-generating composition and the skin-side surface sheet.

6. A face-wearing humidifier according to claim 1, wherein the heat-generating composition comprises metal powder, a salt, a water retention agent and moisture.

7. A face-wearing humidifier according to claim 6, wherein the heat-generating composition comprises carbon for facilitating oxidation of the metal powder.

* * * * *